United States Patent [19]

Kuzmak et al.

[11] Patent Number: 4,592,339
[45] Date of Patent: Jun. 3, 1986

[54] GASTRIC BANDING DEVICE

[75] Inventors: Lubomyr I. Kuzmak, South Orange, N.J.; Frederick L. Coe, Santa Barbara, Calif.

[73] Assignee: Mentor Corporation, Minneapolis, Minn.

[21] Appl. No.: 743,951

[22] Filed: Jun. 12, 1985

[51] Int. Cl.$^4$ ............................................. A61B 19/00
[52] U.S. Cl. ..................................... 128/1 R; 128/346
[58] Field of Search ............... 128/1 R, DIG. 25, 346, 128/325, 327

[56] References Cited

U.S. PATENT DOCUMENTS

| | | | |
|---|---|---|---|
| 3,730,186 | 5/1973 | Edmunds et al. | 128/325 |
| 3,744,063 | 7/1973 | McWhorter et al. | 128/1 R X |
| 4,133,315 | 1/1979 | Berman et al. | 128/303 |
| 4,217,889 | 8/1980 | Radovan et al. | 128/1 |
| 4,246,893 | 1/1981 | Berson | 128/1 R |
| 4,403,604 | 9/1983 | Wilkinson et al. | 128/1 R |
| 4,458,681 | 7/1984 | Hopkins | 128/346 |
| 4,485,805 | 12/1984 | Foster, Jr. | 128/1 |
| 4,501,264 | 2/1985 | Rockey | 128/1 |

OTHER PUBLICATIONS

Solhaug, "Gastric Banding—A New Method in the Treatment of Morbid Obesity", *Current Surg.*, Nov.–Dec. '83, pp. 424–428.

Jama (Medical News) Oct. 1982, vol. 248, No. 16, pp. 1939, 1943.

Check, "Yet Another Variation on Surgery for Obesity," *The Journal of the American Medical Assn.*, vol. 248, No. 16, pp. 1939, 1943, Oct. 22/29, 1982.

Joffe et al, "A Review: Surgery for Morbid Obesity," *Jour. Surg. Sci.*, vol. 33, pp. 74–88, 1982.

Mason et al, "Optimizing Results of Gastric Bypass," *Ann. Surg.*, vol. 182, No. 4, pp. 405–414, Oct. 1975.

Mason et al, "Risk Reduction in Gastric Operations for Obesity," *Ann. Surg.*, vol. 190, No. 2, pp. 158–165, Aug. 1979.

Freeman et al, "Surgery for Morbid Obesity—Where Are We Going?", *The Canadian Journal of Surgery*, vol. 25, No. 3, pp. 247–248, May 1982.

Freeman et al, "Failure Rate with Gastric Partitioning for Morbid Obesity," *The American Journal of Surgery*, vol. 145, pp. 113–119, Jan. 1983.

Reed, "Bad and Good News on Gastroplasty," *Journal of the American Medical Association*, Medical News, vol. 248, No. 3, pp. 277–278, Jul. 16, 1982.

Mason, "Vertical Banded Gastroplasty for Obesity," *Arch. Surg.*, vol. 117, pp. 701–706, May 1982.

Wilkinson entitled "Gastric (Reservoir) Reduction for Morbid Obesity," *Arch. Surg.*, vol. 116, pp. 602–605, May 1981.

*Primary Examiner*—Dalton L. Truluck
*Attorney, Agent, or Firm*—Kinney & Lange

[57] ABSTRACT

A gastric band device for forming a stoma opening in a stomach for treatment of morbid obesity includes a flexible substantially nonextensible band portion having an expandable section that is expandable and deflatable through an injection site. After the nonextensible band portion has been positioned around the stomach to form the stoma opening, the expandable section is used to adjust the diameter of the stoma opening.

10 Claims, 7 Drawing Figures

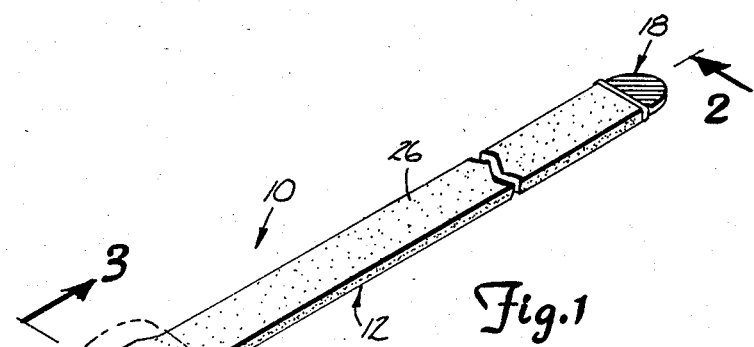
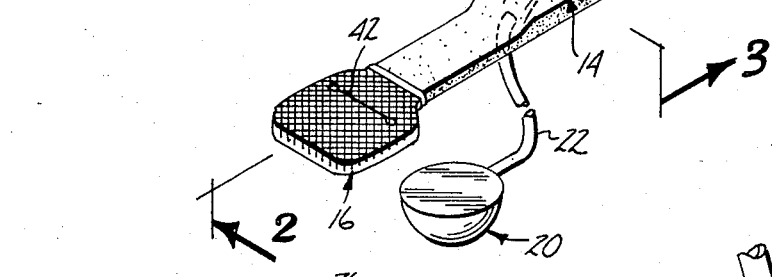
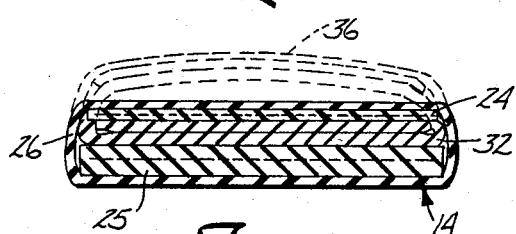
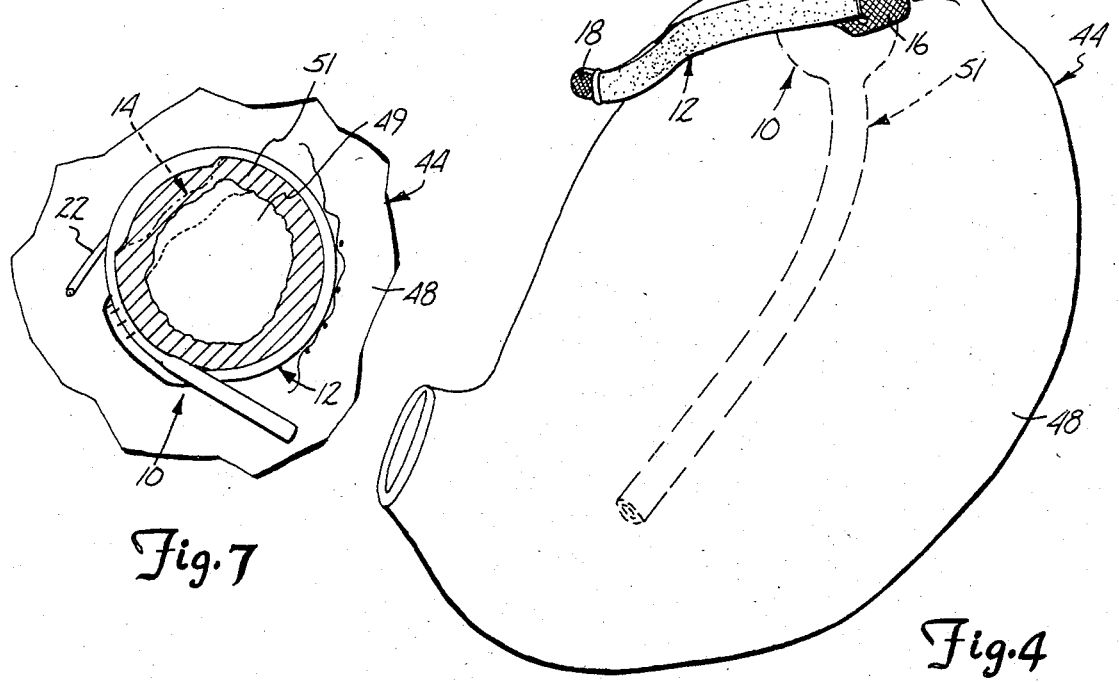

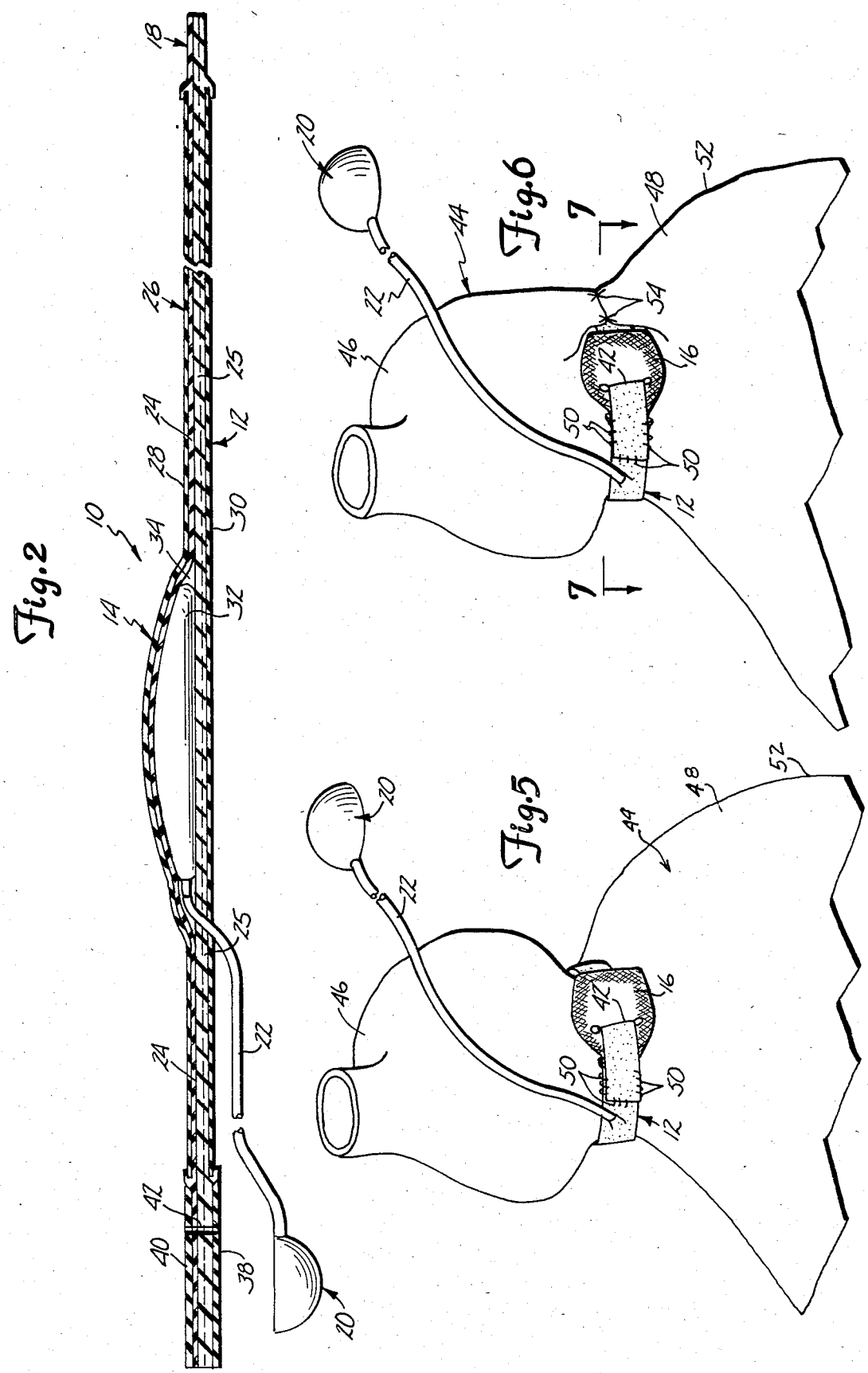

GASTRIC BANDING DEVICE

BACKGROUND OF THE INVENTION

1. Field of the Invention

The present invention relates to a device for the treatment of morbid obesity, and in particular, it relates to gastric banding devices that encircle a portion of the stomach to form a stoma opening of lesser diameter.

2. Description of the Prior Art

Morbid obesity is a condition that is associated with a multitude of other hazards to health that include reduced life expectancy and has even been associated with serious sociopsychologic and economic problems. Dietary management of morbid obesity has not been a successful manner of treatment. In response to the failure of dietary management, various surgical techniques have been developed and used to try to treat morbid obesity.

One method that has been used in the prior art to treat morbid obesity has been referred to as a gastric bypass. The term gastric bypass has been used to describe several different procedures. Some of these procedures are described in articles by Joffe et al, "A Review: Surgery for Morbid Obesity," *Jour. Surg. Sci.*, Vol. 33, pp. 74–88, 1982; Mason et al, "Optimizing Results of Gastric Bypass," *Ann. Surg.*, Vol. 182, No. 4, pp. 405–414, October 1975; and Mason et al, "Risk Reduction in Gastric Operations for Obesity," *Ann. Surg.*, Vol. 190, No. 2, pp. 158–165, August 1979. Gastric bypass has been considered by some as a procedure having considerable risks.

Stapling of portions of the stomach has also been used to treat morbid obesity. This includes both vertical and horizontal stapling and other variations trying to reduce the size of the stomach or make a small stoma opening. Stapling has been described by Freeman et al, "Surgery for Morbid Obesity—Where Are We Going?" *The Canadian Journal of Surgery*, Vol. 25, No. 3, pp. 247–248, May 1982; Freeman et al, "Failure Rate with Gastric Partitioning for Morbid Obesity," *The American Journal of Surgery*, Vol. 145, pp. 113–119, January 1983; Reed, "Bad and Good News on Gastroplasty," *Journal of the American Medical Association*, Medical News, Vol. 248, No. 3, pp. 277–278, July 16, 1982; Mason et al, "Risk Reduction in Gastric Operations for Obesity," *Ann. Surg.*, Vol. 190, No. 2, pp. 158–165, August 1979; and Mason, "Vertical Banded Gastroplasty for Obesity," *Arch. Surg.*, Vol. 117, pp. 701–706, May 1982. Many problems have been associated with the use of staples, first as being undependable, second as causing perforations, and third that the pouch or stoma opening formed by the staples becomes enlarged over time making the procedure useless.

Another method that has been developed is the placement of an inflatable bag or balloon into the stomach causing the recipient a "full feeling." This procedure has been described in the Berman et al U.S. Pat. No. 4,133,315 and the Foster, Jr. U.S. Pat. No. 4,485,805. This procedure, although simple, can also result in the stomach further expanding and making the placement of the bag useless.

Still another procedure includes the placement of a sleeve or a wrap on the inside of the stomach or covering the stomach in the outside. The Rockey U.S. Pat. No. 4,501,264 describes a medical sleeve that is placed on the inside of the stomach which interferes with the digestive or absorption function of the zone in which the sleeve is placed. The wrap which is placed around the stomach is described in the Wilkinson et al U.S. Pat. No. 4,403,604 and in an article by Wilkinson entitled "Gastric (Reservoir) Reduction for Morbid Obesity," *Arch. Surg.*, Vol. 116, pp. 602–605, May 1981.

Still another method includes the placement of a band around a portion of the stomach creating a stoma opening that is less in diameter than the stomach for restricting food intake into the lower digestive portion of the stomach. The band is made of a nonextensible material and is located on the outside of the stomach thereby prohibiting the stoma opening to expand. This banding procedure has been described in articles by Solhaug, "Gastric Banding: A New Method in the Treatment of Morbid Obesity," *Current Surgery*, pp. 424–428, November—December 1983; and Check, "Yet Another Variation on Surgery for Obesity," *Journal of the American Medical Association*, Vol. 248, No. 16, pp. 1939, 1943, Oct. 22/29, 1982. Although the banding procedure has great promise due to its simplicity and the fact that it retains the diameter of the stoma opening, there have been problems in obtaining a proper size stoma opening.

SUMMARY OF THE INVENTION

The present invention includes a gastric band device for creating a stoma opening in a stomach and permits adjustment of the stoma opening after implantation. The device includes a flexible substantially nonextensible band portion having an expandable section that is expandable and deflatable through an injection site.

The expandable section is used to adjust the size of the stoma opening. If the patient is not losing weight as expected, the expandable section is further expanded by injecting a fluid into the injecting site thereby increasing the size of the expandable section and decreasing the size of the stoma opening. The decrease in the size of the stoma opening further restricts the flow of food into the lower digestive portion of the stomach. If the patient is receiving inadequate nutrition and the weight loss is too great, the expandable section is incrementally deflated by withdrawing fluid from the injection site, thereby increasing the size of the stoma opening and increasing the flow of food into the lower stomach portion.

BRIEF DESCRIPTION OF THE DRAWINGS

FIG. 1 is a perspective view of the device of the present invention.

FIG. 2 is a cross sectional view taken along the line 2—2 in FIG. 1 with portions shown whole for purposes of clarity.

FIG. 3 is a cross sectional view taken along the line 3—3 in FIG. 1.

FIG. 4 is a perspective view of the device being initially placed in position around a stomach.

FIG. 5 is a perspective view of the device prior to suturing of the greater curvature to retain the device.

FIG. 6 is a perspective view showing the device in place with the greater curvature sutured.

FIG. 7 is a cross sectional view taken along the line 7—7 in FIG. 6.

DETAILED DESCRIPTION OF THE PREFERRED EMBODIMENTS

A gastric band device of the present invention is generally indicated at 10 in FIGS. 1 and 2. The device 10 includes a longitudinal substantially nonextensible band portion 12, an expandable section 14, a buckle portion 16, a guide tab portion 18, and an injection site 20 fluidly connected to the expandable section 14 by tubing 22.

The band portion 12 preferably includes two central layers 24, 25 made of a Dacron mesh material embedded in a medical grade silicone polymer. The layers 24, 25 are encased in a room temperature vulcanizing silicone polymer layer 26 that extends from the buckle portion 16 to the tab portion 18, as best illustrated in FIG. 1. The layer 26 provides a covering that rounds the longitudinal edges of the band portion. The layers 24, 25 are adhered to each other through their entire length except expandable section 14. Preferably, a strip of Teflon is placed between the layers 24 and 25 defining the expandable section and prevents the layers 24 and 25 from bonding to each other in the expandable section during the vulcanization process. The layers 24, 25 extend through the buckle portion 16, the band portion 12 and the tab portion 18, to provide the device 10 of the present invention with a nonextensible characteristic.

The expandable section 14 includes an inflatable balloon 32 made of a silicone polymer and disposed between the layers 24 and 25. The balloon 32 is preferably at least partially filled with an physiologically compatible fluid, such as a saline solution. The balloon 32 is inflated and deflated by piercing the injection site 20 with a hypodermic needle and either adding or withdrawing fluid. It will be understood that the expandable section can also be constructed having an integral expansion chamber.

As the balloon is filled with saline solution, directional expansion occurs on a side 28 of the band portion 12, as illustrated in FIG. 2. The directional expansion is accomplished by layer 24 being thinner than layer 25.

The expandable section 14 expands as far as the layer 24 permits with the inflatable portion taking the shape that the layer 24 permits, as illustrated in FIG. 3. The layer 24, being made of a nonextensible material, defines the outer limits that the expandable section 14 is expanded. The section 14 expands in a manner such that a substantially flat surface 36 presses against the outer wall of the stomach.

The tubing 22 is made of a medical grade polymer. The tubing extends into the band portion on a side 30 opposite from the side 28. The injection site 20 is well known, being described in the Radovan et al U.S. Pat. No. 4,217,889 and the Schulte U.S. Pat. No. 4,190,040, which are hereby incorporated by reference.

In one working embodiment, the expandable section is located approximately 3 cm from the buckle portion and is approximately 3 cm in length and slightly over 1 cm wide. The balloon is approximately 3 cm long, 1 cm wide, and 3 mm. thick. The tubing is approximately 12 inches long and the injection site is approximately 0.6 inches in diameter. The base, from buckle portion to tab portion, is approximately 8¾ inches long. When fully inflated, the expandable section presents a bulge on the side 28 that is approximately 1 mm thick.

The buckle portion 16 includes the Dacron mesh layers 24 and 25 with additional outside Dacron mesh layers 38 and 40, as illustrated in FIG. 2, all bonded to each other. The buckle portion further includes a slot 42 which extends through the buckle portion. The portion 16 is preferably wider than the band portion 12 for ease of handling during implantation, however, the particular form of the buckle is not important to the present invention.

The tab portion 18 is formed of the layers 24 and 25 extending past the silicone covering 26. In a preferred form, the tab portion 18 is flat with an arcuate edge, although any other configuration is within the scope of the present invention. The purpose of the tab portion 18 is to facilitate insertion of the end of the band portion 12 through the slot 42 of the buckle portion 16. The tab portion 18 is thinner than the band portion 12 and is more easily pushed through the slot 42 and is sufficient in length so it extends through the slot. The tab portion is then gripped on an opposite side of the buckle portion and the band portion is pulled through the slot.

Referring to FIG. 4, the device 10 is positioned to encircle a stomach 44 and separate the stomach into an upper pouch 46 and a lower digestive stomach portion 48. A stoma opening 49 is formed between the upper pouch 46 and the lower stomach portion 48, as illustrated in FIGS. 4 and 6. The device 10 is positioned so that the side 28 and the expandable section 14 rests against an exterior stomach wall 51. The tab portion 18 is placed through the slot 42 so that it extends through the slot. The tab portion 18 is either gripped by hand or gripped by an instrument, such as a surgical pliers, and the band portion 12 is pulled through the slot.

The size of the stoma opening can be determined as described in the article by Solhaug entitled "Gastric Banding: A New Method in the Treatment of Morbid Obesity," *Current Surgery*, pp. 424–428, November–December 1983, using a calibration instrument such as a balloon, as generally indicated by 51 in FIG. 4.

The band portion 12 is pulled through the slot 42 until the desired size of the stoma opening is formed. Once the desired form of the stoma opening is formed, the excess of the band portion extending past the buckle portion is cut off and overlapping sections of the band portion 12 are sutured to each other as indicated by reference character 50 in FIG. 5. At this point, the buckle portion 16 may also be cut at the slot 42 to remove the buckle.

To prevent the device 10 from moving out of position, the device 10 is retained in position by suturing the greater curvature 52 of the stomach on both sides of the band portion 12 to itself with about three or four sutures 54. The retaining of the device 10 in position is important since the size of the upper portion 46 of the stomach determines the amount of food that the patient will consume in any one sitting and receive a "full" feeling and movement of the device would change the size of the upper portion 46. The stoma opening regulates the flow of fluid from the upper portion of the stomach to the lower portion of the stomach and consequently controls the rate of ingestion by the patient.

Once the device 10 is in place, the calibration tube is removed. The injection site is then anchored subcutaneously at a convenient location and the patient allowed to recover.

Typically, the stoma opening formed is approximately 12 to 13 mm. in diameter. The device 10 of the present invention permits adjustment of the stoma opening after the implantation. If the patient is ingesting too much food and does not show the desired weight loss, the expandable section is expanded to decrease the size of the stoma opening. The injection site is pierced through the skin using a hypodermic and additional saline solution is added to the device 10. If the stoma opening is too small and the patient is suffering from a lack of nutrition, the stoma opening is increased by piercing through the skin the injection site 20 and withdrawing saline solution from the device. Withdrawal of saline solution will deflate the portion 14, increasing the size of the stoma opening. Preferably, the device 10 is implanted with the balloon partially filled with saline solution so that the portion 14 is deflatable.

In summary, the device 10 of the present invention provides a permanent implant that controls the amount of food ingested by a patient having morbid obesity. The size of the stoma opening may be adjusted without need of further surgery to regulate the flow of food within the stomach of the patient.

Although the present invention has been described with reference to preferred embodiments, workers skilled in the art will recognize that changes may be mde in form and detail without departing from the spirit and scope of the invention.

What is claimed is:

1. A gastric band device for forming a stoma opening in a stomach comprising:
    a longitudinal flexible substantially nonextensible band portion for encircling the stomach and for partitioning the stomach into a smaller upper portion and a larger lower portion;
    means for securing said band to said stomach wall;
    an expandable section located on the band portion adapted for positioning against a stomach wall; and
    injection site means in fluid connection with the expandable section wherein the expandable section is expandable or deflatable to decrease or increase the size of the stoma opening by addition or withdrawal of fluid through the injection site means.

2. The device of claim 1 wherein the nonextensible band portion has first and second ends and further including buckle means for engagement of the nonextensible band portion during implantation.

3. The device of claim 2 wherein the buckle means includes a slot through which the nonextensible band portion is passed.

4. The device of claim 3 and further including a tab portion attached to the second end of the band portion for introduction of the band portion through the slot.

5. The device of claim 1 wherein the expandable section includes a balloon fluidly connected to the injection site means for inflation and deflation to expand and deflate the expandable section.

6. The device of claim 1 wherein the band portion includes first and second nonextensible layers attached to each other except in the expandable section such that the first and second layers are separated from each other by a fluid.

7. The device of claim 6 wherein an inflatable balloon is disposed between the first and second layers and is fluidly connected to the injection site means.

8. The device of claim 7 wherein the first layer is thinner than the second layer so that the expandable section bulges the first layer outwardly.

9. The device of claim 1 wherein the expandable section is positioned on the side of the band portion adapted to face a stomach wall, the expandable section being expandable toward a direction of the stomach wall.

10. A method for forming a stoma opening, the method comprising:
    implanting a substantially nonextensible band having an expandable section adapted for receiving a fluid such that the expandable section rests proximate an exterior surface of the stomach; and
    adding to or withdrawing from the expandable section the fluid to expand the expandable section to decrease the stoma opening or to deflate the expandable section to increase the stoma opening.

* * * * *